[54] 1-SUBSTITUTED HYDROXYIMINOMETHYL-PYRIDINIUM SALTS, WITH AN ACTIVITY AGAINST ORGANOPHOSPHATE POISONINGS

[75] Inventors: Hendrik P. Benschop, Pijnacker; Larry A. Kepner, Delft; Leonardus P. A. de Jong, Bleiswijk, all of Netherlands

[73] Assignee: Nederlandse Centrale Organisatie Voor Toegepast-Natuurwetenschappelij-konderzoek, The Hague, Netherlands

[21] Appl. No.: 170,625

[22] Filed: Jul. 21, 1980

[30] Foreign Application Priority Data

Jul. 26, 1979 [NL] Netherlands ............ 7905789

[51] Int. Cl.$^3$ .................. A61K 31/38; A61K 31/425; A61K 31/44

[52] U.S. Cl. ..................... 424/263; 424/10; 424/2

[58] Field of Search ............ 546/280, 333, 264; 544/333; 424/251, 263, 10, 2

[56] References Cited

U.S. PATENT DOCUMENTS 2,996,510  8/1961  Green ..................... 260/294.8

FOREIGN PATENT DOCUMENTS 6717412  6/1968  Netherlands .
6717413  6/1968  Netherlands .
6917153  5/1970  Netherlands .
7704030  10/1977  Netherlands .
1210519  10/1970  United Kingdom .

OTHER PUBLICATIONS de Jong, *Chemical Abstracts*, vol. 91, Entry 104323c, (1979).
Karlsson et al., *Acta Chem. Scand.*, vol. 27, pp. 224–2246 (1973).
Simeon et al., *Chem. Abstracts*, vol. 80, entry 116869w (1974).
Benschop et al., *Chem. Abstracts*, vol. 86, entry 26689g (1977).
Grifantini et al., *Jour. of Pharm. Sci.*, vol. 61, pp. 631–633 (1970).
Hegedorn et al., *Angew. Chem. Int. Ed.*, vol. 11, pp. 307–309 (1972).
Franchetti et al., *Il. Farmaco-Ed. Sc.*, vol. 29, pp. 309–316 (1974).
Watthey et al., *J. Org. Chem.*, vol. 38, pp. 4170–4172 (1973).
Patocka, *Chem. Abstracts*, vol. 82, entry 108126c (1975).
Brown et al., *Jour. of the Amer. Chem. Soc.*, vol. 98, pp. 5682–5688 (1976).
Guendel, *Chem. Abstract*, vol. 87, entry 2297u (1977).
Schoene et al., *Chem. Abstracts*, vol. 80, entry 628n (1974).
Steinberg et al., *Chem. Abstracts*, vol. 87, entry 12699x (1977).
Patocka, *Coll. Czech. Chem. Comm.*, vol. 38, pp. 2996–3003 (1973).
Reiner et al., *Chem. Abstracts*, vol. 79, entry 78553h (1973).
Milosevic et al., *Chem. Abstracts*, vol. 61, entry 2419b (1964).
Wolthius et al., *Chem. Abstracts*, vol. 87, entry 195063z (1977).
Oldiges, *Chem. Abstracts*, vol. 86, entry 51255v (1977).

*Primary Examiner*—John M. Ford
*Attorney, Agent, or Firm*—Hammond & Littell, Weissenberger and Muserlian

[57] ABSTRACT 1-substituted hydroxyiminomethyl-pyridinium salts, a process for the production of said compounds, compositions with an activity against organophosphate poisonings, and a process for the preparation of such compositions.

The invention provides 1-substituted hydroxyiminomethyl-pyridinium salts of the formula 4, wherein $R_1$ is a substituted or unsubstituted (hetero) aryl group or a corresponding dihydro group,
$R_2$ is a hydrogen, an alkyl or aryl group,
$R_3$ is hydrogen or an alkyl group and
$Z^-$ is an anion suited for pharmacological purposes, pharmacological composition containing said compounds and a process for the preparation of said compounds by reacting a pyridine carboxaldoxime with a (hetero) arylhalide. The compounds in question show a good activity against nerve gases and are suited for prophylaxis too.

4 Claims, 4 Drawing Figures

1.
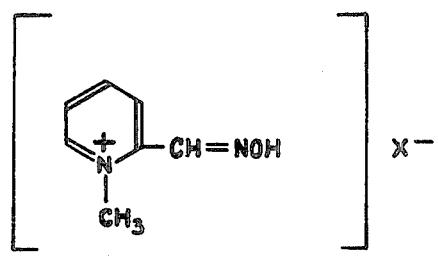
2.
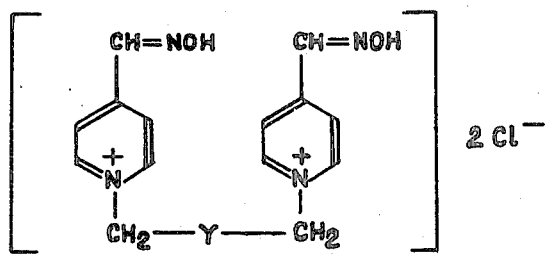
3.
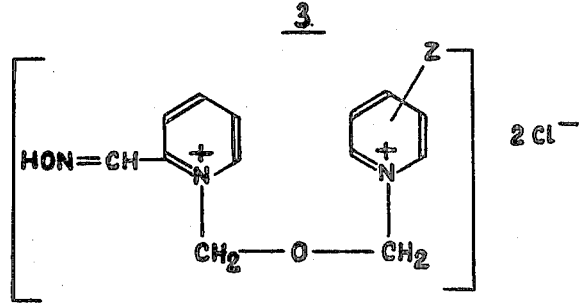
4.
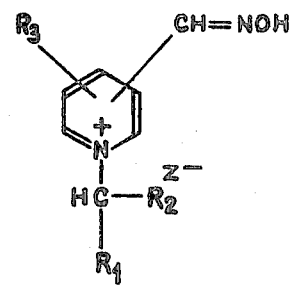

1-SUBSTITUTED HYDROXYIMINOMETHYL-PYRIDINIUM SALTS, WITH AN ACTIVITY AGAINST ORGANOPHOSPHATE POISONINGS

The invention relates to 1-substituted hydroxyiminomethyl pyridinium salts, to a process for the production of said compounds, to compositions with an activity against organophosphate poisonings containing said compounds and to a process for the preparation of said compositions.

The last 25 years a number of oxime derivatives with cholinesterase-reactivating activity have been developed for therapeutical use in organophosphate poisonings. Said organophosphates can be both pesticides (parathion e.g.) and the so-called "nerve gases" (sarin, VX, tabun e.g.). The toxic activity of said compounds is mainly caused by the blocking of the transmission of the nerve impulses from the parasympathetic and sympathetic nerve system to the muscles in the body, by means of inhibiting the acetylcholinesterase enzyme. Some oximes are capable of removing the inhibition by a chemical reaction with the organophosphate radical on the enzyme, that is a causal therapy.

At present, four products are available for practical use. The first two oximes are 1-methyl-2-hydroxyiminomethyl pyridinium salts (formula 1 of the formula sheet) wherein $X=Cl^-$:pralidoxime (see Bull. Org. Mond. Santé, 1971, 44, 289–307) and $X=MeSO_3^-$:P2S (see Journal of Pharmaceutical Sciences, 61 1136–1140) 1972)).

Further two symmetric bisquaternary pyridinium derivatives are known in which the two oxime groups occupy the 4-positions of the pyridinium rings (formula 2, wherein $Y=CA_2$:TMB4; and $Y=O$:toxogonin (see Arch. Toxical, 36, 71–81, 1976).

Very recently a number of asymmetric bisquaternary pyridinium derivatives have been disclosed in which only one oxime group occupies the 2-position of one of both pyridinium rings (see formula 3, wherein e.g. $Z=-4-C(O)NH_2, -3-C(O)$phenyl, $-3-C(O)$cyclohexyl).

The monoquaternary pyridinium oximes of the formula 1 are beneficial in that they (i) show a good therapeutical activity against sarin, VX, and a great number of pesticides, and (ii) result in an active blood level on oral administration so that they are also useful for oral prophylaxis. The oximes of the formula 1, wherein X has the definition indicated above, are disadvantageous in that they are only effective in a high dosis (about 10 mg/kg i.m.). Said high doses require very high oxime concentrations (25–50% weight by weight) in the autoinjectors with which some armies are equipped for self and comrade relief in case nerve gases might be used in wartime. Said high concentrations cause problems as to the stability during storage, strong pain during intramuscular injection and a substantial necrosis of the muscular tissue at the site of the injection. It has further been mentioned that the oximes of formula 1 exhibit scarcely any positive influence in poisonings with the nerve gases tabun and soman, although there have also not any detrimental influences on the poisoning.

The symmetric bisquaternary pyridinium oximes of formula 2 in which Y has the definition indicated above are beneficial in that (i) they are therapeutically active in considerably lower doses than the compounds of the formula 1, so that the above indicated problems with respect to the high oxime concentrations in the autoinjectors of said compounds are considerably less serious, (ii) exhibit a good therapeutic activity against the nerve gas tabun, in contrast to the compounds of the formula 1, while the compounds of the formula 2 also show a good therapeutic activity against organophosphates against which the compounds of formula 1 are active too. Disadvantages of the compounds of formula 2, in which Y has the definition indicated above, are that (i) they are scarcely resorbed from the gastrointestinal tract so that an oral prophylactic use is not possible, and (ii) it is assumed that administration of said oximes after poisoning with the nerve gas soman may be detrimental to the intoxication, resulting from the toxicity and relatively great stability of said reaction products of formula 2 with said nerve gas, wherein Y has the definition indicated above.

The oximes of formula 3 are characterized by their specific therapeutic activity against soman.

It has now been found that a new type of monoquaternary pyridinium oximes, viz. 1-(hetero)arylmethylhydroxyiminomethyl pyridinium salts of formula 4, wherein $R_1$ is substituted or unsubstituted (hetero)aryl or a corresponding dihydrogroup, $R_2$ is hydrogen, an alkyl or aryl group, $R_3$ is hydrogen or an alkyl group and $Z^-$ is an anion suited for pharmacological purposes, show substantially the same favorable properties of the compounds of the formulae 1 and 2, described above, wherein X and Y have the definitions given above, and on the other hand do not exhibit the adverse properties of said oximes.

The compounds of the present invention in which the oxime radical is in the 2-position are preferred. Further $R_1$ represents preferably an unsubstituted phenyl or a 3-thiazole group and $R_2$ is preferably a hydrogen atom.

The oximes of the invention are, in low doses, therapeutically active against, e.g., sarin.

Furthermore the oximes of the invention exhibit a therapeutic activity which is distinctly better than that of the compounds of the formula 2, wherein X has the definition indicated above, against organophosphates containing a phosphoros-nitrogen bond. The oximes of the invention exhibit good protection against, among others, tabun, sarin and paraoxon after oral, prophylactic administration.

As with the compounds of the formula 1, wherein X has the definition indicated above, the present oximes are active against the nerve gas soman, however, do not exhibit a detrimental influence on the poisoning with soman, in contradistinction to the compounds mentioned above of the formula 2. Finally it should be indicated that the $LD_{50}/ED_{50}$-ratio of the oximes of the invention is more favorable than that of the compounds of the formula 1, which have been described.

The compounds of the invention do not seriously influence the blood pressure. Tests indicated only a slight increase of the blood pressure.

The invention further encompasses pharmacological compositions containing a compound of the invention as an active component. Said compositions can be produced according to any method known per se. Suitable administration forms are tablets and solutions. Solutions can be administered, e.g. by means of an auto-injector.

The invention is further illustrated by means of the following examples, which are only given for illustration and should in no way limit the invention.

EXAMPLE I

A method of production A

The production of 1-benzyl-2-hydroxyaminomethyl-pyridinium bromide (compound 1).

A mixture of 25.7 grams (115 mmoles) benzyl bromide and 16.7 grams (137 mmoles) 2-hydroxyiminomethyl-pyridine in dimethyl formamide (70 ml) was stored 7 days at room temperature. The precipitate was filtered off and washed with ethanol and ether. Recrystallization from 96% ethanol yielded 30.9 gram (77%) of the compound 1 in the form of white crystals. (a) In case (hetero)arylmethyl chlorides were used instead of bromides or iodides the reaction mixture was heated at 60°-90° C. for 3 to 4 hours. (b) Cyclohexylmethyl iodide alkylated 2-hydroxyiminomethylpyridine with great difficulty. After reaction at 100° C. for 10 hours a product was precipitated with ether. Recrystallisation yielded a mixture of compound 30 and of the hydroiodide of 2-hydroxyiminomethyl-pyridine from which the compound 30 could be recovered by washing with water.

EXAMPLE II

A method of production B

The production of 1-benzyl-2-hydroxyiminomethyl-pyridinium methanesulphonate (compound 4)

A solution of 15.5 g (76.5 mmols) silver methanesulphonate in 50 ml of water (prepared from silver hydroxide freshly precipitated with NaOH, and 10% of an substoechiometric amount of 10% of methanesulphonic acid in aceton-itrile) was added to 22.4 g (76.5 moles) of compound 1 dissolved in 250 ml of water at 70° C. whilst stirring. After 10 minutes stirring with activated carbon (Norit) at 70° C. the reaction mixture was filtered, and the colourless filtrate was subsequently dried. The residual oil became crystalline after the addition of acetone and subsequent evaporation of the solvent under vacuum. After washing with ether and drying the colourless compound 4, which appeared to be free from bromide, was obtained.

EXAMPLE III

Production method C

The production of 1-(β-phenethyl)-2-hydroxyiminomethyl-pyridinium iodide (compound 19).

A solution of 23.2 g (100 mmoles) β-phenethyl iodide and of 24.4 g (200 mmoles) 2-hydroxyiminomethylpyridine in ethanol (100 ml) was refluxed during 24 hours. The solvent was evaporated and the residue was treated with 250 ml diethyl ether/acetone (1/3) yielding a yellow precipitate. Said precipitate was filtered off and was subsequently recrystallised from ethanol/acetone (7/2) to which ether was added in portions until a ratio ethanol/acetone/diethyl ether 7/2/2 (weight/weight) was obtained.

EXAMPLE IV

The production of tablets

Tablets were prepared from:
(1) 500 g of compound 4
(2) 100 mg of starch
(3) 3% solution of methylcellulose q.s.
(4) 25 mg of talcum
(5) 5 mg magnesiumstearate The ingredients (1) and (2) were mixed and 150 ml of (3) was added and the mixture was agitated using supportum 33.

The product obtained was dried at 30°-40° C. and (4) and (5) were added through sieve bottom 24. After mixing the product was pressed to 1000 tablets of 535 mg have a diameter of 13 mm.

EXAMPLE V 1000 tablets were produced from the following ingredients:
(1) 500 g of the active compound 24
(2) 75 g potato starch
(3) 25 g polyvitonum
(4) 10 g glycerol
(5) 100 g aqua
(6) 20 g talcum
(7) 5 g magnesiumstearate To produce tablets (1) and (2) were comminuted together and (3) was dissolved in a mixture of (4) and (5). The powder was moistened with about 75 ml. of said solution. The mixture was passed through a sieve bottom 30 and dried during about 5 hours at 30°-40° C. and the dried granules were passed through a sieve bottom 30. A mixture of (6) and (7) was added through sieve bottom 24, the product was mixed and tablets of 620 mg each having a diameter of 40 mm were pressed.

A mixture of 10 g (100 mmole) 4-methyl-isothiazole, 18 g (101 mmole) N-bromosuccinimide and 0.5 g (2.1 mmole) dibenzoyl peroxide in dry carbon tetrachloride (250 ml) was refluxed for 3 hours. The reaction was followed by $^1$H-KSR and was stopped when too much dibromation (of the methylgroup) occured. After that the reaction was stopped the ratio of starting material:-monobrominationproduct:dibrominationproduct was about 25:65:10 ($^1$H-KSR).

After standing overnight the precipitate was filtered off and the filtrate was subsequently evaporated dry under vacuum. Diethyl ether (50 ml) was added to the impure, red brown coloured product. After filtration 12.2 g (100 mmole) 2-hydroxyiminomethylpyridine and dimethyl formamide (25 ml) were added to the filtrate and the ether was subsequently evaporated under vacuum. The mixture was stored during the weekend at ambient temperature and the precipitate formed was subsequently filtered off and washed with acetone and ether. Finally a recrystallisation from ethanol (96%) yielded the compound 25 (7.7 g, 26%) of a colourless product.

The compounds enumerated in table A have been prepared according to the method indicated in said table.

From the compounds indicated in table A the compounds of the formulae 4,24,22,16 and 8 are preferred.

The activity of the compounds of the invention was tested according to the following method.

TABLE A

Production and analysis of 1-(hetero)arylmethylhydroxyiminomethyl-pyridinium salts of the formule 4

| compound | structure R₁ | R₂ | R₃ | Oxime pos. | Z⁻ | method of production | yield (%) | melting point (°C) | Mol. weight | weight % C calc/found | weight % H calc/found | weight % N calc/found | weight % Hal calc/found | weight % S calc/found |
|---|---|---|---|---|---|---|---|---|---|---|---|---|---|---|
| 1 | phenyl | H | H | 2 | Br⁻ | A | 77 | 206.0–206.5 | 293.17 | 53.26 / 53.33–53.34 | 4.47 / 4.43–4.46 | 9.56 / 9.55–9.56 | 27.26 / 27.05–27.11 | — |
| 2 | phenyl | H | H | 3 | Br⁻ | A | 64 | 171.5–172.0 | 293.17 | 53.26 / 53.51–53.52 | 4.47 / 4.36–4.36 | 9.56 / 9.44–9.45 | 27.26 / 26.83–26.84 | — |
| 3 | phenyl | H | H | 4 | Br⁻ | A | 70 | 193.0–195.0 | 293.17 | 53.26 / 52.79–52.84 | 4.47 / 4.61–4.63 | 9.56 / 9.47–9.48 | 27.26 / 27.00–27.00 | — |
| 4 | phenyl | H | H | 2 | CH₃SO₃⁻ | B | 99 | 173.0–174.5 | 308.35 | 54.53 / 54.14–54.17 | 5.23 / 5.20–5.24 | 9.09 / 9.10–9.11 | — | 10.40 / 10.34–10.36 |
| 5 | phenyl | H | H | 2 | n-BuSO₃⁻ | B | 69 | 148.5–149.0 | 350.94 | 58.26 / 57.97–58.02 | 6.33 / 6.11–6.20 | 8.00 / 8.01–8.06 | — | 9.15 / 8.88–8.95 |
| 6 | 2-Me-phenyl | H | H | 2 | Br⁻ | A | 72 | 172.5–173.5 | 307.20 | 54.74 / 54.73–54.82 | 4.92 / 4.90–4.93 | 9.12 / 9.05–9.08 | 26.01 / 25.91–25.96 | |
| 7 | 3-Me-phenyl | H | H | 2 | Br⁻ | A | 48 | 195.0–196.0 | 307.20 | 54.74 / 54.71–54.78 | 4.92 / 4.94–4.96 | 9.12 / 9.13–9.18 | 26.01 / 25.96–26.03 | |
| 8 | 4-Me-phenyl | H | H | 2 | Br⁻ | A | 67 | 214.0–214.5 | 307.20 | 54.74 / 54.66–54.75 | 4.92 / 4.83–4.87 | 9.12 / 9.06–9.08 | 26.01 / 25.79–25.81 | |
| 9 | 4-MeO-phenyl | H | H | 2 | Cl⁻ | A | 8 | 160.0–161.0 | 278.74 | 60.33 / 60.11–60.15 | 5.42 / 5.38–5.41 | 10.05 / 9.96–10.01 | 12.72 / 12.51–12.52 | |
| 10 | 4-Cl-phenyl | H | H | 2 | Cl⁻ | A | 8.5 | 185.0–185.5 | 283.16 | 55.14 / 55.02–55.17 | 4.27 / 4.29–4.36 | 9.90 / 9.85–9.88 | 25.05 / 24.85–24.90 | |
| 11 | 4-O₂N-phenyl | H | H | 2 | Cl⁻ | A | 3.6 | 169.1–170.0 | 293.71 | 53.16 / 52.76–52.84 | 4.12 / 4.04–4.13 | 14.31 / 14.16–14.22 | 12.07 / 11.89–11.95 | |

TABLE A-continued

Production and analysis of 1-(hetero)arylmethylhydroxyiminomethyl-pyridinium salts of the formula 4

| compound | structure R₁ | R₂ | R₃ | Oxime pos. | Z⁻ | method of production | yield (%) | melting point (°C.) | Mol. weight | weight % C calc/found | weight % H calc/found | weight % N calc/found | weight % Hal calc/found | weight % S calc/found |
|---|---|---|---|---|---|---|---|---|---|---|---|---|---|---|
| 12 |  | H | H | 2 | I⁻ | A | 16 | 182.1–182.5 | 591.94 | 26.38 / 26.97–27.01 | 1.87 / 2.19–2.30 | 4.73 / 4.58–4.60 | 64.31 / 61.15–61.39 | |
| 13 |  | H | H | 2 | Cl⁻ | A | 11 | 186.0–186.5 | 316.72 | 53.09 / 52.44–52.53 | 3.82 / 3.89–3.93 | 8.85 / 8.82–8.84 | 11.20(Cl) / 11.11–11.13 | 18.00(F) / 17.69–17.72 |
| 14 |  | H | H | 2 | 2I⁻ | A | 17 | >170 | 525.18 | 36.59 / 36.35–36.41 | 4.03 / 4.26–4.30 | 8.00 / 7.84–7.87 | 48.33 / 47.65–47.68 | |
| 15 |  | H | H | 2 | Br⁻ | A | 56 | 202.3–203.1 | 343.22 | 59.49 / 59.37–59.46 | 4.41 / 4.45–4.45 | 8.16 / 8.05–8.09 | 23.28 / 22.95–23.00 | |
| 16 |  | H | Et | 2 | Br⁻ | A | 44 | 207.0–207.5 | 321.22 | 56.08 / 56.14–56.16 | 5.33 / 5.25–5.28 | 8.72 / 8.61–8.64 | 24.88 / 24.55–24.57 | |
| 17 |  | | H | 2 | Br⁻ | A | 60 | 137.2–137.9 | 369.26 | 61.80 / 61.81–61.89 | 4.64 / 4.55–4.74 | 7.59 / 7.51–7.56 | 21.64 / 21.64–21.58 | |
| 18 | | Me | H | 4 | Br⁻ | A | 50 | 168.5–170.1 | 307.20 | 54.74 / 54.68–54.70 | 4.92 / 4.98–5.04 | 9.12 / 9.19–9.22 | 26.01 / 25.69–25.71 | |
| 19 |  | H | H | 2 | I⁻ | C | 22 | 185.2–186.9 | 354.18 | 47.47 / 48.01–48.05 | 4.27 / 4.25–4.32 | 7.91 / 7.89–7.89 | 35.83 / 35.79–35.83 | |
| 20 |  | H | H | 2 | 2Br⁻ | A | 60 | 238.3–239.1 | 508.22 | 47.26 / 47.18–47.24 | 3.97 / 4.03–4.04 | 11.03 / 10.73–10.85 | 31.45 / 30.37–30.40 | |

TABLE A-continued

Production and analysis of 1-(hetero)arylmethylhydroxyiminomethyl-pyridinium salts of the formula 4

| compound | structure R₁ | R₂ | R₃ | Oxime pos. | Z⁻ | method of production | yield (%) | melting point (°C.) | Mol. weight | Element analysis calc/found weight % C | weight % H | weight % N | weight % Hal | weight % S |
|---|---|---|---|---|---|---|---|---|---|---|---|---|---|---|
| 21 | OX-⁺N-CH₂-⟨C₆H₄⟩- | H | H | 4 | 2Br⁻ | A | 75 | 290.5–291.5 | 508.22 | 47.26 / 47.16–47.22 | 3.97 / 3.93–3.97 | 11.03 / 10.85–10.92 | 31.45 / 30.82–30.80 | |
| 22 | thiophene-2-yl | H | H | 2 | Cl⁻ | A | 31 | 173.0–173.5 | 254.74 | 51.86 / 51.86–51.90 | 4.35 / 4.38–4.43 | 11.00 / 10.91–10.98 | 13.92 / 13.80–13.81 | 12.59 / 12.59–12.63 |
| 23 | furan-2-yl | H | H | 2 | Cl⁻ | A | 8 | 152–153 | 238.68 | 55.36 / 55.00–55.00 | 4.65 / 4.72–4.74 | 11.74 / 11.51–11.53 | 14.85 / 14.60–14.62 | |
| 24 | isothiazol-3-yl | H | H | 2 | Br⁻ | D | 13 | 197.1–198.5 | 300.18 | 40.01 / 39.86–39.86 | 3.36 / 3.27–3.39 | 14.00 / 13.88–13.89 | 26.62 / 26.72–26.76 | 10.68 / 10.71–10.71 |
| 25 | isothiazol-5-yl | H | H | 2 | Br⁻ | D | 26 | 197.5–198.0 | 300.18 | 40.01 / 39.96–40.03 | 3.36 / 3.28–3.31 | 14.00 / 13.90–13.99 | 26.62 / 26.65–26.67 | 10.68 / 10.69–10.72 |
| 26 | thiazol-2-yl | H | H | 2 | Cl⁻ | A | 9 | 178.0–178.5 | 255.73 | 46.24 / 46.24–46.29 | 4.02–4.06 | 16.05–16.06 | 13.67 / 13.67–13.69 | 12.82 / 12.82–12.8 |
| 27 | 6-methylpyridin-2-yl | H | H | 4 | Cl⁻ | A | 45 | 203.0–203.5 | 249.70 | 57.72 / 57.61–57.64 | 4.84 / 4.80–4.91 | 16.83 / 16.67–16.69 | 14.20 / 14.11–14.13 | |
| 28 | imidazolium | H | H | 4 | 2Cl⁻ | A | 68 | 234.5–235.0 | 275.14 | 43.65 / 42.13–42.23 | 4.40 / 4.43–4.44 | 20.36 / 19.95–20.00 | 25.77 / 25.63–25.65 | |
| 29 | 4-methylphenyl | H | H | 2 | Cl⁻ | A | 9 | 170.2–171.9 | 250.73 | 62.28 / 62.08–62.14 | 6.03 / 5.90–5.94 | 11.17 / 11.28–11.34 | 14.14 / 14.01–14.03 | |

Reactivating capability of 1-(hetero)arylmethyl-hydroxyiminomethyl-pyridinium salts (IV)

Method

Inhibited bovineerythrocyte acetylcholinesterase was obtained by the following method:

(a) a mixture of a solution of about 2 mg enzyme (Sigma Chemical Comp. St. Louis, U.S.A.)/ml in 6.6 mM veronal buffer, pH 7.5 with an equal volume of a solution of 0.05 $\mu$M VX, 0.1 $\mu$M tabun, 0.3 $\mu$M paraoxon or 0.4 $\mu$M mevinphos respectively, in the same buffer was incubated at 25° C. for 1, 1, 2½ or 17½ hours respectively;

(b) a mixture of a solution of 2 mg enzyme/ml in 6.6 mM veronal buffer, pH 9.0 with an equal volume of a 0.2 $\mu$M sarin solution in the same buffer was incubated at 0° C. for 100 minutes;

(c) a mixture of 100 volumes of a solution of 3.9 mg enzume/ml in 6.6 mM veronal buffer, pH 7.5, containing 0.1 M KCl with one volume of a 31 mM methamidophos solution in isopropanol or with two volumes of a 35 mM crufomate solution in isopropanol was incubated at 25° C. for 1 and 2 hours respectively. The excess of organo-phosphate was removed by extracting the enzyme-organo-phosphate mixture three times with ether (1½:1 vol/vol), and the enzyme solution was subsequently kept under vacuum for thirty minutes to remove the greater part of the ether. The excess of methamidophos and crufomate was removed by gel-filtration on Sephadex G-25. The solution of inhibited enzyme in 6.6 mM veronal buffer, pH 7.5, containing 0.1 M KCl obtained from the solution was diluted with the solvent to an enzyme concentration of 1.3 mg/ml.

The reactivation was started by the addition of one volume of an oxime solution in 40 mM phosphate buffer, pH 7.5, to four volumes of the solution of the inhibited enzyme, the pH of which had been adjusted at 7.5. For the study of the reactivation of the inhibited enzyme in the absence of oxime only phosphate buffer was added to the inhibited enzyme solution. Reactivation studies were done at 25° C. for 24 hours. Each 60–100 min. the enzyme activity in a one ml sample of the reactivation mixture ($AIR_t$) was determined automatically by means of a pH-stat titration. The determination of the activity was done at pH 7.5 and 25° C. with 23 ml of a 3.2 mM acetylcholine perchlorate solution in 0.1 M KCl. The titrant was 0.05 N NaOH. Enzyme activities were corrected for spontaneous hydrolysis of the substrate. Blank values for the activity of the enzyme (A), of the enzyme incubated with the oxime (AR) and of the inhibited enzyme (AI) were determined also.

The percentage reactivation at time t ($\%$ reactivity$_t$) was calculated as follows:

$$\% \text{ react}_t = \frac{AIR_t \frac{A}{AR} - AI}{A - AI} \cdot 100 \quad (1)$$

Velocity constants of the reactivation process ($k_{obs}$) and the maximum percentage of reactivation ($\%$ react$_\infty$) were calculated as follows:

$$\% \text{ react}_t = \% \text{ react}_\infty (1 - e^{-k_{obs}t}) \quad (2)$$

Said equation 2 was evaluated by means of the smallest least squares method from $\%$ react$_t$ data obtained at different t-values.

RESULTS

Data concerning the reactivating ability of the compounds of the invention with respect to the tabun-inhibited acetylcholinesterase are indicated in table B. Data concerning the reactivating ability of one representative of the compounds of the invention 1-benzyl-2-hydroxyiminomethyl-pyridinium methanesulphonate (4) obtained from experiments in which acetyl cholinesterases were inhibited by several organophosphates have been indicated in table C. For comparison, data obtained with three known reactivators of the formulae 1 and 2 have been inserted in said table too.

TABLE B

Reactivation of tabun-inhibited acetyl cholinesterase with 10 $\mu$M of compound of the formula IV at pH 7.5 and 25° C.: percentage reactivation ($\%$ react) after 2 hours and the velocity constant of the reactivation process ($K_{obs}$) calculated from the reactivation data and the maximum percentage of reactivation ($\%$ react$_\infty$).

| compound nr. | % react after 2h | $k_{obs}$ ($10^{-3}$min$^{-1}$) | % react$_\infty$ |
|---|---|---|---|
| 1 | 48 | 6.7 ± 0.1 | 87.3 ± 0.2 |
| 2 | 1 (a) | <0.1 | — |
| 3 | 3 (a) | <0,1 | — |
| 4 | 40 | 5.4 ± 0.1 | 86.7 ± 0.4 |
| 5 | 41 | 5.83 ± 0.09 | 82.7 ± 0.2 |
| 6 | 13 | 1.6 ± 0.1 | 72 ± 2 |
| 7 | 23 | 2.72 ± 0.04 | 79.7 ± 0.3 |
| 8 | 28 | 3.44 ± 0.06 | 83.2 ± 0.4 |
| 9 | 2 | 0.44 ± 0.12 | 48 ± 10 |
| 10 | 19 | 2.33 ± 0.05 | 76.6 ± 0.5 |
| 11 | 5 | 0.77 ± 0.04 | 58 ± 2 |
| 12 | 12 | 1.62 ± 0.06 | 69 ± 1 |
| 13 | 4 | 0.69 ± 0.04 | 48 ± 2 |
| 14 | 5 (a) | <0.1 | — |
| 15 | 11 | 1.39 ± 0.03 | 72 ± 1 |
| 16 | 39 | 4.94 ± 0.05 | 86.5 ± 0.2 |
| 17 | 7 | 1.06 ± 0.04 | 60 ± 1 |
| 18 | 4 (a) | <0.1 | — |
| 19 | 3 | 0.60 ± 0.04 | 45 ± 2 |
| 20 | 12 | 1.38 ± 0.06 | 76 ± 2 |
| 21 | 33 | no first order | |
| 22 | 38 | 4.78 ± 0.09 | 88.2 ± 0.3 |
| 23 | 15 | 1.78 ± 0.06 | 73 ± 1 |
| 24 | 51 | 7.5 ± 0.1 | 86.8 ± 0.2 |
| 25 | 9 | 1.24 ± 0.04 | 65 ± 1 |
| 26 | 10 | 1.38 ± 0.03 | 66 ± 1 |
| 27 | 3 (a) | <0.1 | — |
| 28 | 2 (a) | <0.1 | — |
| 29 | 33 | 3.98 ± 0.07 | 85.4 ± 0.4 |
| P$_2$S | 3 | 0.55 ± 0.06 | 36 ± 3 |
| TMB$_4$ | 41 | no first order | |
| Toxonogin | 28 | no first order | |

(a) percentage reactivation after 24 hours.

TABLE C

Percentage reactivation of organophosphate-inhibited acetylcholinesterase incubation with 10 $\mu$M oxime at pH 7.5 and 25° C. for 2 and 24h

| Oxim Organo-phosphate | 4 2h 24h | P$_2$S 2h 24h | TMB$_4$ 2h 24h | Toxonogin 2h 24h | spontaneous reactivation 2h 24h |
|---|---|---|---|---|---|
| VX | 30 95 | | | | 10 (18h) |
| sarin* | 20 65 | 35 70 | 45 85 | 45 85 | |
| tabun | 48 87 | 3 19 | 41 77 | 28 71 | |
| monitor | 70 100 | 65 95 | 90 100 | 90 100 | 90 |
| crufomate | 76 98 | 57 100 | 53 91 | 48 94 | 10 |
| paraoxon | 35 95 | 30 90 | 70 90 | 75 90 | 13 |
| mevinphos | 37 47 | | | | 18 43 |

*reactivator concentration 5 $\mu$M

"IN VIVO" RESULTS

Experimental data

Atropine sulphate (PH.NED.VI) was obtained from Brocades-Stheeman and Pharmacia, Amsterdam.

All test animals were bred in the Medical Biological Laboratory TNO. The mice belong to the hybrid CC57 strain and weighed about 18 g. The rats belong to the WAG strain and weighed about 170 g. Only female animals were used. All doses indicated are in milliliters or in milligrams per kilogram of body weight (ml/kg or mg/kg, resp.).

The test animals used in experiments in which the oxime was administered orally were deprived of food the night before. The oximes were dissolved in demineralized water. Said solutions were administered in a volume of 5 ml/kg body weight.

The organophosphates were administered subcutaneously in the form of solutions in demineralized water (2.5 ml/kg). Tabun, however, was administered in an aquous solution containing up to 7% (vol/vol) propylene glycol, while paraoxon was administered in dimethyl sulfoxide (1 ml/kg).

In therapeutic experiments with atropine sulfate or with combinations of atropine sulfate and oximes, solutions of said substances in demineralized water were administered intraperitoneally in a volume of 1 ml/kg for rats and 10 ml/kg for mice.

For intravenous administration the oximes were dissolved in water containing 0.9% (weight/vol) of sodium chloride.

Statistical analysis of the results

The number of surviving animals was determined 7 days after each test. Dose-response relations were calculated by means of the probit/log dose method. Said relations were tested for linearity and for the significance of the regression.

The value indicated in the tables as "relative protection" was calculated after an additional test for the parallelity of the dose-response curves. The ratio $LD_{50}/ED_{50}$ is the arithmetic ratio of said values, as obtained from two non-parallel curves.

Results

The toxicities of the organophosphates used are enumerated in table D, while the toxicities of the oximes are indicated in table E. The oximes 1 and 4 are significantly more toxic after intravenous or intraperitoneal administration than the compounds of the formula 1, wherein X represents the $MeSO_3^-$ group. This might suggest that 1 and 4 exhibit a greater affinity for the active centre of acetyl cholinesterase than $P_2S$. Both $P_2S$ and 4 are considerably less toxic after oral administration, which suggests that only a limited absorption from the gastrointestinal tract occurs after ingestion of said substances.

On oral administration it appears that 4 is a more effective prophylactic against tabun than the conventional oximes $P_2S$ and Toxogonin (table F). The prophylactic activity of 4 against sarin and paraoxon is comparable in value with that of $P_2S$. Neither oxime 4 nor $P_2S$ are prophylactically active against soman.

In oral prophylaxis against a fixed dose of tabun it appears that a considerably smaller dose of 4 is required than of $P_2S$ to protect 50% of the animals (table G).

It further appears that 4 is not only an effective prophylactic but also a therapeutic for the poisoning with organophosphates. It appears from table H that a considerably smaller dose of 4 than of $P_2S$ is required to save 50% of the animals after a tabun poisoning. The calculated value $LD_{50}/ED_{50}$ is about three times better for the oxime 4 than for $P_2S$.

From experiments comparable to the experiments mentioned in table H, wherein the oximes $P_2S$ and 4 were administered i.p. together with atropine sulfate 1.5 min. after 0.5 mg/kg s.c. sarin, it can be estimated that the effective therapeutic dose (50% survival) of $P_2S$ and of 4 against 0.5 mg/kg sarin is 0.5 (0.3–0.8) and 0.3 (0.1–0.8) mg/kg. The estimated slopes of the dose response curves, however, were so low ($-1$ and $-0.6$ probits/log, resp.) that the $ED_{50}$-values could not be determined with sufficient accuracy. Said low slopes of the dose-response curves are probably due to the very rapid action of the nerve gas sarin so that the 1.5 min. pause between the administration of sarin and of oxime is too long to permit build up of an effective oxime blood level. After a sufficient blood level has been obtained both oximes show a good activity against sarin (see table F).

TABLE D

Toxicity of organo-phosphates in rats after subcutaneous administration

| organophosphate | $LD_{50}$(mg/kg) 95% confidence interval |
|---|---|
| tabun | 0.35 (0.29–0.37) |
| sarin | 0.16 (0.15–0.16) |
| soman | 0.13 (0.12–0.15) |
| paraoxon | 0.39 (0.38–0.40) |

TABLE E

Toxicity of oximes.

| oxime | animal | method of administration | $LD_{50}$(mg/kg) (95% confidence interval) | slope (probits/ log) |
|---|---|---|---|---|
| $P_2S$ | rat | i.v. | 109[x] | |
| $P_2S$ | rat | i.p. | 260 (250–270) | 31 |
| $P_2S$ | rat | i.p.[xx] | 140 (130–150) | 15 |
| $P_2S$ | rat | oral | 3700[xx] | |
| $P_2S$ | mouse | i.p. | 170 (170–180) | 24 |
| 1 | rat | i.p. | 37 (36–38) | 44 |
| 1 | mouse | i.p. | 31 (29–33) | 21 |
| 4 | rat | i.v. | 16 (15–17) | 17 |
| 4 | rat | i.p. | 29 (17–30) | 28 |
| 4 | rat | i.p.[xx] | 26 (25–27) | 34 |
| 4 | rat | oral[xxx] | 1400 (1000–1800) | 3,9 |

[x]literature value, see JPRS 53.615: July 16, 1971
[xx]37.5 mg/kg atropine sulfate was administered together with the oxime
[xxx]Volume of administration 10 ml/kg

TABLE F

Oral prophylaxis against organophosphates in rats. The oximes
(100 mg/kg) were administered orally, 30 minutes before the administration (s.c.) of organo-phosphate. Altropine sulfate (37.5 mg/kg) was
administered (i.p.) to all animals 1.5 minutes after the administration
of the organo-phosphate.

| Organo-phosphate | Prophy-laxis | $LD_{50}$ org.phosph. (mg/kg) (95% confidence interval) | Slope probits/log | relative protection (95% confidence interval) |
|---|---|---|---|---|
| tabun | phys.salt solution | 0.32(0.30–0.34) | 23 | |
| | $P_2S$ | 0.68(0.60–0.74) | 13 | (1.0) |
| | Toxonogin | 0.97(0.84–1.10) | 7.7 | 1.5(1.2–1.8) |
| | 4 | 4.0(3.6–4.8) | 7.3 | 6.0(5.1–7.2) |
| sarin | phys.salt solution | 0.19(0.18–0.21) | 15 | |
| | $P_2S$ | 0.76(0.65–0.90) | 6.9 | (1.0) |
| | 4 | 0.59(0.52–0.66) | 8.1 | 0.78(0.64–0.93) |
| soman | phys.salt solution | ca. 0.15 | | no indications of a measurable effect with any oxime. |
| | $P_2S$ | ca. 0.15 | | |
| | 4 | ca. 0.15 | | |
| paraoxon | phys.salt solution | ca. 7 | | |
| | $P_2S$ | ca. 130 | | |
| | 4 | ca. 90 | | |
| monitor | phys.salt solution | | | |
| | $P_2S$ | | | |
| | 4 | | | |

TABLE G

Effective oral doses of the oximes $P_2$ S and 4 against tabun
in rats. The oximes were administered 30 minutes before the
administration of tabun (s.c. 0.6 mg/kg).
Atropine sulfate was administered 1.5 minutes after tabun (i.p.).

| Oxime | $ED_{50}$ of the oxime (mg/kg) (95% confidence interval) | Slope probits/log |
|---|---|---|
| $P_2S$ | 30(20–45) | −2.5 |
| 4 | 7.8(5.3–10.2) | −3.1 |

TABLE H

Therapy with the oximes $P_2$ S and 4 after intoxication with tabun.
The oximes were administered together with atropine sulfate (i.p.)
1.5 minutes after tabun (s.c., 1 mg/kg).

| Oxime | $ED_{50}$ of the oxime (mg/kg) (95% confidence interval) | Slope probits/log |
|---|---|---|
| $P_2S$ | 19(14–24) | −3.8 |
| 4 | 1.2(0.99–1.4) | −6.3 |

TABLE I

"Safety ratios" of the oximes $P_2$ S and 4 in the therapy of
intoxication. The ratio indicated is that of the $LD_{50}$ of the oxime
(in the presence of atropine sulfate, see table E) to that of the
$ED_{50}$ of the oxime in tabun intoxication therapy (see table H).

| Oxime | $LD_{50}/ED_{50}$ |
|---|---|
| $P_2S$ | 7.4 |
| 4 | 22 |

APPENDIX Structure of the organo-phosphates mentioned in the text
tabun = O—ethyl-N,N—dimethylphosphoramid-ocyanidate, $EtO(Me_2N)P(O)CN$.
sarin = O—isopropyl-methylphosphonfluoridate-, iPrO(Me)P(O)F
soman = O—pinalkyl-methylphosphonfluoridate PinO(Me)P(O)F
VX = O—ethyl-S—2-diisopropylaminoethyl-methylphosphonthioate, $EtO(Me)P-(O)SCH_2CH_2N(iPr)_2$.
paraoxon = O,O—diethyl-O—p-nitrophenyl-phosphate, $(EtO)_2P(O),OC_6H_4$—p-$NO_2$
methamidophos = monitor = O,S—dimethyl-phosphosphoramidothioate, MeO(MeS)P(O)NH2·
crufomate = O—2-chloro-4-t-butylphenyl-O—methyl-N—methylphosphoramidate, $MeO(MeNH)P(O)OC_6H_3$—o-Cl—p-tBu.
mevinphos = dimethyl—O,O—dimethyl-O—(1-methyl-2-carbomethoxy)vinyl-phosphate, (phosdrin) $(MeO)_2P(O)OC(Me) = CH(COOMe)$

We claim:
1. A method of protecting and treating warm-blooded animals from organophosphate poisoning comprising administering to warm-blooded animals an amount of at least one compound of the formula

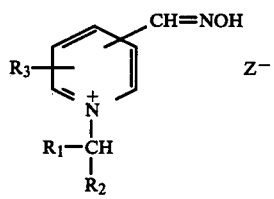

wherein $R_1$ is selected from the group consisting of benzyl, thiophenyl and isothioazolyl optionally substituted with at least one member selected from the group consisting of methyl, methoxy, chloro, iodo, —$NO_2$, —$CH_3$ and

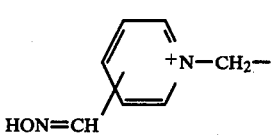

$R_2$ is selected from the group consisting of hydrogen, methyl and phenyl, $R_3$ is selected from the group consisting of hydrogen, and ethyl and Z is a non-toxic, pharmaceutically acceptable anion sufficient to prevent or treat organophosphate poisoning.

2. The method of claim 1 wherein Z is selected from the group consisting of halogen and lower alkyl sulfonate.

3. The method of claim 1 wherein $R_1$ is thiophenyl, $R_2$ and $R_3$ are hydrogen, Z is $Cl^-$ and the oxime group is in the 2-position.

4. The method of claim 1 wherein $R_1$ is 3-isothiazolyl, $R_2$ and $R_3$ are hydrogen, Z is $Br^-$ and the oxime group is in the 2-position.

UNITED STATES PATENT AND TRADEMARK OFFICE
CERTIFICATE OF CORRECTION

PATENT NO. : 4,352,810
DATED : October 5, 1982
INVENTOR(S) : HENDRIK P. BENSCHOP ET AL.

It is certified that error appears in the above-identified patent and that said Letters Patent is hereby corrected as shown below:

Title page, line 6 of Abstract; Column 1, line 7; Column 3,
          line 11 and 53; Column 12, line 10:
              "hydrox-" should read -- hydroxy- --.
Title page, line 7 of Abstract; Column 7, line 8; Column 3,
          line 12 and 54; Column 12, line 11:
              "yiminomethyl" should be -- iminomethyl --.
Column 15, line 61: "phosphosphoramidothioate" should read
              -- phosphoramidothioate --.
Column 15, line 63: "mevinphos = dimethyl-0,0-dimethyl" should be
              -- mevinphos = 0,0-dimethyl --.

Signed and Sealed this

Twelfth Day of April 1983

[SEAL]

Attest:

GERALD J. MOSSINGHOFF

Attesting Officer    Commissioner of Patents and Trademarks